(12) United States Patent  
Whittenburg et al.

(10) Patent No.: US 12,347,434 B1
(45) Date of Patent: *Jul. 1, 2025

(54) SYSTEMS AND METHODS FOR REAL-TIME PATIENT RECORD TRANSCRIPTION AND MEDICAL FORM POPULATION VIA MOBILE DEVICES

(71) Applicant: JPJ Ventures, LLC, Nashville, TN (US)

(72) Inventors: Daemon Whittenburg, Carrolton, GA (US); Pat Williams, Nashville, TN (US); Justin Hipps, Nashville, TN (US)

(73) Assignee: JPJ Ventures, LLC, Nashville, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/495,078

(22) Filed: Oct. 26, 2023

Related U.S. Application Data

(63) Continuation of application No. 17/136,273, filed on Dec. 29, 2020, now Pat. No. 11,837,224, which is a (Continued)

(51) Int. Cl.
*G10L 15/00* (2013.01)
*G06F 9/54* (2006.01)
(Continued)

(52) U.S. Cl.
CPC .............. *G10L 15/22* (2013.01); *G06F 9/547* (2013.01); *G10L 15/1822* (2013.01);
(Continued)

(58) Field of Classification Search
None
See application file for complete search history.

(56) References Cited

U.S. PATENT DOCUMENTS 7,624,027 B1 11/2009 Stern et al.
7,752,035 B2 7/2010 Oon
(Continued)

OTHER PUBLICATIONS

Notice of Allowance for U.S. Appl. No. 17/136,273, mailed Aug. 22, 2023, 7 Pages.

*Primary Examiner* — Satwant K Singh
(74) *Attorney, Agent, or Firm* — Bradley Arant Boult Cummings LLP; Daniel E. Sineway, Esq.

(57) ABSTRACT

Systems and methods for real-time patient record transcriptions and medical form population via mobile devices are described. A user (e.g., a medical professional) may speak into or near a mobile device operable to detect or record spoken language, and furthermore the mobile device may initiate real-time transcription of the spoken language to generate unstructured transcription text data corresponding to the spoken language. The unstructured transcription text data may be parsed for words or phrases indicative of medical information for generating structured data, where the structured data includes terms, phrases, and values identified via delineators and/or natural language processing techniques. Discrete data from the structured data may be directly inserted into corresponding locations (e.g., appropriate medical form text fields) in electronic medical records via APIs and service bus relays.

20 Claims, 7 Drawing Sheets

Related U.S. Application Data continuation of application No. 16/176,429, filed on Oct. 31, 2018, now Pat. No. 10,909,985.

(60) Provisional application No. 62/579,503, filed on Oct. 31, 2017.

(51) Int. Cl.
  *G10L 15/18* (2013.01)
  *G10L 15/22* (2006.01)
  *G10L 15/30* (2013.01)
  *G16H 10/60* (2018.01)
  *H04L 9/32* (2006.01)
  *H04L 9/40* (2022.01)

(52) U.S. Cl.
  CPC ............ *G10L 15/30* (2013.01); *G16H 10/60* (2018.01); *H04L 9/3213* (2013.01); *H04L 63/0485* (2013.01); *H04L 63/166* (2013.01)

(56) References Cited

U.S. PATENT DOCUMENTS

| | | | |
|---|---|---|---|
| 8,000,984 B2 | 8/2011 | Hasan et al. | |
| 8,260,635 B2 | 9/2012 | Hasan et al. | |
| 8,606,594 B2 | 12/2013 | Stern et al. | |
| 8,850,057 B2 | 9/2014 | Natoli et al. | |
| 8,886,521 B2 | 11/2014 | Patch | |
| 9,569,593 B2 | 2/2017 | Casella Dos Santos | |
| 9,569,594 B2 | 2/2017 | Casella Dos Santos | |
| 9,785,753 B2 | 10/2017 | Casella Dos Santos | |
| 9,842,188 B2 | 12/2017 | Stern et al. | |
| 9,996,664 B2 | 6/2018 | Lloyd et al. | |
| 10,199,124 B2 | 2/2019 | Casella Dos Santos | |
| 10,909,985 B1 * | 2/2021 | Whittenburg | G10L 15/30 |
| 10,978,192 B2 * | 4/2021 | Casella Dos Santos | G16H 10/60 |
| 11,398,232 B1 * | 7/2022 | Agassi | G10L 15/22 |
| 11,837,224 B1 * | 12/2023 | Whittenburg | G16H 10/60 |
| 2001/0053986 A1 | 12/2001 | Dick | |
| 2004/0068545 A1 | 4/2004 | Daniell et al. | |
| 2005/0138210 A1 | 6/2005 | Shkvarchuk et al. | |
| 2007/0016450 A1 | 1/2007 | Bhora et al. | |
| 2008/0046292 A1 | 2/2008 | Myers et al. | |
| 2009/0222283 A1 | 9/2009 | Lassetter et al. | |
| 2011/0106564 A1 | 5/2011 | Hachmeister et al. | |
| 2012/0173281 A1 | 7/2012 | DiLella et al. | |
| 2015/0332011 A1 | 11/2015 | Ting et al. | |
| 2016/0063191 A1 | 3/2016 | Vesto et al. | |
| 2017/0228500 A1 | 8/2017 | Massengale | |
| 2017/0344948 A1 | 11/2017 | Kumar | |
| 2018/0101647 A1 | 4/2018 | Lloyd et al. | |
| 2018/0315428 A1 * | 11/2018 | Johnson | G10L 15/26 |
| 2019/0121532 A1 * | 4/2019 | Strader | G16H 80/00 |
| 2019/0259480 A1 | 8/2019 | Casella | |

* cited by examiner

SYSTEMS AND METHODS FOR REAL-TIME PATIENT RECORD TRANSCRIPTION AND MEDICAL FORM POPULATION VIA MOBILE DEVICES

CROSS REFERENCE TO RELATED APPLICATIONS

This application is a continuation patent application of U.S. patent application Ser. No. 17/136,273, now issued U.S. Pat. No. 11,837,224, filed on Dec. 29, 2020, and entitled "SYSTEMS AND METHODS FOR REAL-TIME PATIENT RECORD TRANSCRIPTION AND MEDICAL FORM POPULATION VIA MOBILE DEVICES," which is a continuation patent application of U.S. patent application Ser. No. 16/176,429, now issued U.S. Pat. No. 10,909,985, filed on Oct. 31, 2018, and entitled "SYSTEMS AND METHODS FOR REAL-TIME PATIENT RECORD TRANSCRIPTION AND MEDICAL FORM POPULATION VIA MOBILE DEVICES", which claims the benefit of, and priority to, U.S. Provisional Patent Application No. 62/579,503, filed on Oct. 31, 2017, and entitled "SYSTEMS AND METHODS FOR REAL-TIME PATIENT RECORD TRANSCRIPTION AND MEDICAL FORM POPULATION VIA MOBILE DEVICES," and incorporates by reference the same as if they were included herein in their entireties.

TECHNICAL FIELD

The present disclosure relates generally to systems and methods for populating electronic medical records with transcribed and/or normalized data via application programming interfaces.

BACKGROUND

Generally, physicians and other medical professionals manually record medical activity, or other relevant information regarding a patient's health, into an electronic medical record system (e.g., EHR or EMR systems). Traditional electronic medical record systems are typically located on immobile computing systems such as desktop computers and servers. The immobility of traditional electronic health record systems is problematic because it prohibits the physician from interacting with the patient while simultaneously recording the treatment information efficiently and accurately. Furthermore, it is cumbersome and time consuming to manually type information into EHR systems. Not only is manually typing information a time consuming task, but typical EHR systems are also difficult to navigate and generally not user-friendly.

Some aspects of EHR systems allow for data to be "shared" between otherwise closed systems (e.g., siloed data at a particular doctor's office). Generally, closed EHR systems include data formatting standards not compatible with other EHR systems. EHR data may be translated (upon request) between formatting standards to be compatible with other EHR systems, although translating between data formats often requires saved records of rules for determining how to translate the data, which becomes cumbersome when accommodating for many different EHR systems and formatting standards.

Therefore, there exists a long-felt but unresolved need for systems and methods that allow real-time patient record transcription and medical form population via mobile devices, and also systems and methods that allow for improved access to EHR data from external systems.

BRIEF SUMMARY OF DISCLOSURE

The present systems and methods relate generally to real-time patient record transcriptions and medical form population via mobile devices. According to various embodiments, the present systems and methods described herein allow for a physician or other medical professional (e.g., a user) to vocally dictate healthcare information relating to care administered to a particular patient while simultaneously administering the care or treatment, the vocal dictation captured via a mobile device and transcribed in real-time. Included in the present system is a mobile application that may be installed on the user's mobile device(s), and the mobile application may allow for the user to speak within an audible range of the mobile device so that the voice of the user is detected and recorded. In response to recording the user's vocal dictation, the user may select to transmit the recorded vocal dictation to be transcribed in real time by an operatively connected transcriber. In some embodiments, the vocal dictation is transmitted to the transcriber as it is recorded, or the vocal dictation is transmitted automatically upon detecting a stopping point in the dictation.

Consider, for example, a situation where a physician is examining a patient. If the physician's electronic medical record system was immobile (e.g., at a desktop computer), the physician would need to examine the patient and then pause or stop the examination in order to record the examination results into his/her electronic health record system. The present systems and methods allow for the physician to conduct the examination and vocally dictate or describe the care being given, symptoms monitored, prescribed or suggested medications, etc., and his/her mobile device (or a mobile application running at mobile device) may detect, record, and further transmit the information to be transcribed in real-time. According to various aspects of the present disclosure, the real-time dictation-to-transcription systems and methods described herein allow for the physician to deliver care without sacrificing the physician-patient experience.

Furthermore, the present systems allow for data (e.g., the transcribed data) to be automatically inserted or updated into EHRs. The process of entering information into an EHR system is a cumbersome and time consuming task that typically includes manually typing healthcare information according to certain codes/standards, providing accompanying notes for provided care, converting handwritten notes to electronic notes, etc. The systems and methods described herein eliminate the need for such cumbersome tasks, thereby allowing medical professionals to spend less time entering information into a computer and more time providing care. In certain embodiments, this problem is solved via the use of application programming interfaces ("API's") which may be configured to directly access particular data locations within an EHR system. In various embodiments, the system APIs may allow for transcribed data to be automatically inserted in the corresponding patient's EHR, or data from external systems (e.g., a separate doctor's EHR system) may be directly accessed without the need for requesting the data.

In various embodiments, the present disclosure discusses a system for processing spoken language data into an electronic health record ("EHR") system, wherein the EHR system is associated with a healthcare provider and operatively connected to a mobile computing device, the EHR system further including electronic healthcare records associated with a particular patient, and wherein the electronic healthcare records are formatted according to a particular standard, the system including: (a) a mobile computing device associated with the healthcare provider, wherein the mobile computing device detects spoken language and initiates generation of transcription data corresponding to the spoken language, wherein the transcription data includes unstructured text data; and (b) an application programming interface ("API") system, wherein the API system includes one or more API instances operable to: (i) receive the transcription data over a network connection; (ii) parse the transcription data with one or more delineators for generating structured text data, wherein the one or more delineators include preconfigured healthcare terms; (iii) identify discrete data within the structured text data, the discrete data comprising classifiable medical data; and (iv) insert the classifiable medical data into a particular memory location at the EHR system according to the particular standard, wherein the particular memory location corresponds to a form field in the electronic health records associated with the classifiable medical data.

In one embodiment, initiating generation of the transcription data includes transmitting the detected spoken language to a real-time transcription service for transcribing the detected spoken language into the transcription data. In various embodiments, the system further includes an API traffic manager for assigning tasks to the one or more API instances based on a volume of requests received from the mobile computing device. In a particular embodiment, the system may include a remote EHR system not associated with the healthcare provider, wherein particular API instances of the API system access particular memory locations within the remote EHR system. According to various aspects of the present disclosure, prior to inserting the classifiable medical data into a particular memory location at the EHR system, the one or more API instances are further operable to normalize the discrete data into the particular standard.

In certain embodiments, the mobile computing device associated with the healthcare provider is authenticated via an authentication directory at the API system. In a particular embodiment, the mobile computing device associated with the healthcare provider is authenticated via a token included in the transcription data. In one embodiment, the mobile computing device associated with the healthcare provider is authenticated via multi-factor authentication.

In various embodiments, electronic communications with the API system are transmitted via port 443. In one embodiment, the network connection is a TLS encrypted HTTPS network connection. In a particular embodiment, the one or more delineators are determined via natural language processing algorithms trained to identify the particular standard.

According particular embodiments, the present disclosure discusses a cloud-supported system for directly inserting electronic medical data into one or more disparate electronic health record ("EHR") systems, the cloud-supported system including: (a) an application programming interface ("API") traffic manager operable to receive requests, over a network connection, from a healthcare provider computing system for electronic health record data corresponding to a particular patient, wherein the API traffic manager is configured to forward the requests to API processing instances, and wherein healthcare providers at the healthcare provider computing system are authenticated via an authentication directory operatively connected to the API traffic manager;

(b) an API service module comprising the API processing instances and operatively connected to the API traffic manager, wherein the API service module determines an EHR location at an external EHR system including the requested electronic health record data and initiates access to the requested electronic health record data via a service bus relay, wherein the service bus relay is operable to: (i) retrieve the requested electronic health record data from the external EHR system; (ii) initiate normalization of the retrieved electronic health record data according to a standard format; and (iii) directly insert the retrieved electronic health record data, in the normalized standard format, into an EHR system at the healthcare provider computing system.

According to various aspects of the present disclosure, the API traffic manager is operable to forward requests to the API processing instances based on a volume of requests received from the healthcare provider computing system. In certain embodiments, the healthcare providers at the healthcare provider computing system are authenticated via a token included in the requests for the electronic health record data.

In one embodiment, the healthcare providers at the healthcare provider computing system are authenticated via multi-factor authentication. In various embodiments, electronic communications with the API service module are transmitted via port 443. According to various aspects of the present disclosure, the network connection is a TLS encrypted HTTPS network connection.

In a particular embodiment, the present disclosure discusses a method including the steps of: (a) receiving, at an application programming interface ("API") service instance, unstructured transcription text data over a network connection, wherein transmission of the unstructured transcription text data is initiated by a mobile device; (b) parsing the unstructured transcription text data with one or more delineators for generating structured text data, wherein the one or more delineators comprise preconfigured healthcare terms; (c) identifying discrete data within the structured text data, the discrete data comprising classifiable medical data; and (d) inserting the classifiable medical data into a particular memory location at one or more EHR systems via the API service instance.

In certain embodiments, the network connection is a TLS encrypted HTTPS network connection. In particular embodiments, the one or more delineators are determined via natural language processing algorithms trained to identify a particular data format comprising the preconfigured healthcare terms.

These and other aspects, features, and benefits of the claimed embodiment(s) will become apparent from the following detailed written description of the embodiments and aspects taken in conjunction with the following drawings, although variations and modifications thereto may be effected without departing from the spirit and scope of the novel concepts of the disclosure.

BRIEF DESCRIPTION OF DRA WINGS

Further features and benefits of the present disclosure will be apparent from a detailed description of various embodiments thereof taken in conjunction with the following drawings, wherein similar elements are referred to with similar reference numbers, and wherein.

DETAILED DESCRIPTION OF DRAWINGS

The above and further features of the disclosed exemplary systems and methods will be recognized from the following detailed descriptions and drawings of particular embodiments. The present systems and methods relate generally to real-time patient record transcriptions and medical form population via mobile devices. According to various embodiments, the present systems and methods described herein allow for a physician or other medical professional (e.g., a user) to vocally dictate healthcare information relating to care administered to a particular patient while simultaneously administering the care or treatment, the vocal dictation captured via a mobile device and transcribed in real-time. Included in the present system is a mobile application that may be installed on the user's mobile device(s), and the mobile application may allow for the user to speak within an audible range of the mobile device so that the voice of the user is detected and recorded. In response to recording the user's vocal dictation, the user may select to transmit the recorded vocal dictation to be transcribed in real time by an operatively connected transcriber. In some embodiments, the vocal dictation is transmitted to the transcriber as it is recorded, or the vocal dictation is transmitted automatically upon detecting a stopping point in the dictation.

Consider, for example, a situation where a physician is examining a patient. If the physician's electronic medical record system was immobile (e.g., at a desktop computer), the physician would need to examine the patient and then pause or stop the examination in order to record the examination results into his/her electronic health record system. The present systems and methods allow for the physician to conduct the examination and vocally dictate or describe the care being given, symptoms monitored, prescribed or suggested medications, etc., and his/her mobile device (or a mobile application running at the mobile device) may detect, record, and further transmit the information to be transcribed in real-time. According to various aspects of the present disclosure, the real-time dictation-to-transcription systems and methods described herein allow for the physician to deliver care without sacrificing the physician-patient experience.

Furthermore, the present systems allow for data (e.g., the transcribed data) to be automatically inserted or updated into EHRs. The process of entering information into an EHR system is a cumbersome and time consuming task that typically includes manually typing healthcare information according to certain codes/standards, providing accompanying notes for provided care, converting handwritten notes to electronic notes, etc. The systems and methods described herein eliminate the need for such cumbersome tasks, thereby allowing medical professionals to spend less time entering information into a computer and more time providing care. In certain embodiments, this problem is solved via the use of application programming interfaces ("API's") which may be configured to directly access particular data locations within an EHR system. In various embodiments, the system APIs may allow for transcribed data to be automatically inserted in the corresponding patient's EHR, or data from external systems (e.g., a separate doctor's EHR system) may be directly accessed without the need for requesting the data.

Figure 1:
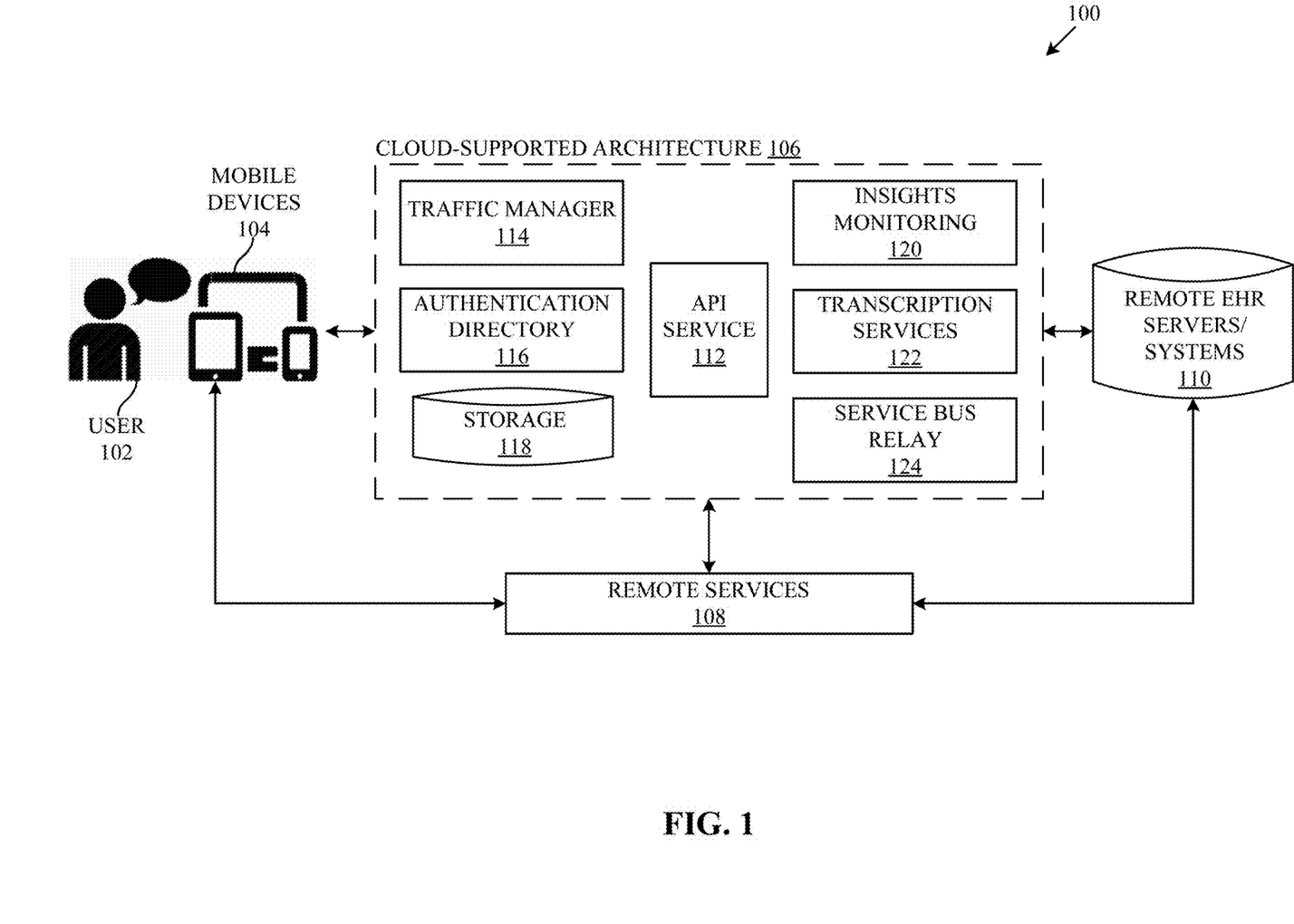
FIG. 1 is a diagram of an exemplary system environment, according to one aspect of the present disclosure.

Referring now to the drawings, FIG. 1 is a diagram of an exemplary system environment 100, according to one aspect of the present disclosure. As shown in the present embodiment, a user 102 (e.g., a doctor, physician, nurse, etc.) may speak near or into one or more mobile computing devices 104 ("mobile devices"), for example, during a medical examination. In certain embodiments, the one or more mobile devices 104 may be smartphones, tablets, smartwatches, or any appropriate computing device with a speaker or microphone for detecting spoken language. According to various aspects of the present disclosure, the user's 102 spoken language may be detected and recorded by the mobile device 104 as the user 102 dictates the medical examination, and furthermore the mobile device 104 may initiate real-time transcription of the spoken language. In certain embodiments, the mobile device 104 may locally transcribe the spoken language (in near real-time), or the mobile device 104 may transmit data corresponding to the spoken language to a cloud-supported architecture 106 or remote services module 108 for transcribing the spoken language (in near real-time). As will be discussed in greater detail herein, transcribing spoken language includes generating unstructured text data corresponding to the user's 102 detected/recorded spoken words. In various embodiments, this unstructured text data may be parsed and converted into structured data including discrete medical data, and the discrete medical data may be directly inserted into EHR systems where appropriate.

In one embodiment, the mobile device 104 may be operatively connected to the cloud-supported architecture 106 over a network connection (e.g., wired/wireless Internet or local network), and the cloud-supported architecture 106 may be hosted on services such as Microsoft® Azure® or Amazon® AWS®, or the cloud-supported architecture 106 may be independently hosted by a particular doctor or hospital. According to various aspects of the present disclosure, the remote services module 108 is also operatively connected to the mobile device 104 and includes services such as real-time transcription services (e.g., MModal), data analytics services, or other appropriate third-party services. In particular embodiments, both the cloud-supported architecture 106 and the remote services module 108 may be operatively connected to remote EHR servers/systems 110, where the remote EHR servers/systems 110 may include EHR servers, SQL databases, external cloud-based EHR APIs, or other appropriate servers and systems.

In particular embodiments, the cloud-supported architecture 106 may provide the system with a plurality of computing resources and tools such as processors, specific processing modules, databases, etc. Accordingly, the cloud-supported architecture 106 may be operatively connected to the mobile devices 104, remote services 108, and remote EHR servers/systems 110, for transmitting and receiving various types of data (e.g., EHR data, transcription data, etc.) between each of those system components. In various embodiments, the cloud-supported architecture 106 includes an API service module 112, where the API service module is a "vertically" and "horizontally" scalable network component including API processing resources for handling transcription data, medical data extracted from the transcription data, direct access to EHR systems, etc. In particular embodiments, the API processing resources may be referred to herein as API instances. In certain embodiments, these API instances may be independent computing resources or threads instantiated for performing particular tasks. In some embodiments, the API instances may be configured to perform any received task/request.

Generally, prior to being received at the API service module 112, data may be received at a traffic manager module 114, where the traffic manager 114 manages incoming traffic (e.g. EHR data, transcription data, XML payloads, etc.) from the one or more mobile devices 104 (or remote servers/systems). In a particular embodiment, the traffic manager 114 is operable to detect, receive, or otherwise monitor the incoming data from the one or more mobile devices 104 and further dynamically optimize the API service 112 based on the incoming data traffic. In one embodiment, the traffic manager 114 executes "health checks" and load balances on the active API instances in the API service module 112 to determine if the current state of the system can effectively handle and process the incoming data. According to particular embodiments, the traffic manager 114 may direct the incoming data to API instances most capable of executing the incoming traffic (e.g., a particular API instance not as busy as others, or a particular API instance better equipped to handle the particular type of traffic, etc.). In some embodiments, if the active API instances are each operating at capacity (or if it is otherwise beneficial to the system), the API service module 112 may instantiate a new API instance to accommodate the incoming traffic. In various embodiments, the API service module 112 may be self-aware and may increase computing capacity or instantiate new API instances (e.g., "scale up" or "scale out") as needed. It should be understood from the discussion herein that the data received at and transmitted from the traffic manager 114 is secure data (e.g., TLS encrypted over HTTPS transmitted via port 443, or the like) for protecting the identities of the associated patients and other sensitive information.

Continuing with FIG. 1, and according to various aspects of the present disclosure, the cloud-supported architecture 106 includes an authentication directory 116 for validating that the incoming data from the traffic manager 114 is being transmitted from a valid user or source (e.g., a registered medical professional, a registered EHR system, etc.). In some embodiments, data transmitted from the mobile device 104 may include authentication credentials (e.g., tokens) that may be used to authenticate the sender's identity via a remote or local directory, such as an Azure® Active Directory®. In some embodiments, the system may support Multi-Factor Authentication (MFA).

In various embodiments, the cloud-supported architecture 106 may include one or more databases or electronic storage mediums for maintaining records of detected/recorded audio (e.g., spoken language), transcription data, discrete medical data, EHR data, etc. As shown in the present embodiment, the system includes at least one database, indicated as storage 118 in the present embodiment, for storing system data. In one embodiment, the storage 118 may include SQL databases for storing electronic health records in various standards (e.g., ICD10, CPT, SNOMED, etc.), transcribed data, and other healthcare information. In certain embodiments, SQL databases allow for the electronic health record data to be stored in a structured and organized fashion for efficient storage and look-up.

According to various aspects of the present disclosure, audio data corresponding to the detected/recorded spoken language may be stored at the storage 118 for maintaining a copy of the data, or for further transmitting the data to other system components such as remote EHR systems or transcription service modules, etc. According to various aspects of the present disclosure, the audio data may be stored in "blob storage" at the storage 118, which is a general storage location for large file formats such as audio files. In a particular embodiment, information relating to the audio data is stored in an SQL format for including data such as EHR metadata, user favorites and preferences, MModal metadata, dictated documents, etc. In one embodiment, the data stored in SQL format may reference the audio file stored in blob storage and allows for the system to maintain structured data corresponding to the data stored in blob storage.

In various embodiments, the cloud-supported architecture 106 may include an insights monitoring module 120 for monitoring activity within the system and logging events such as requests for data, receiving data, run-time exceptions, etc. In one embodiment, monitoring these aspects allows for the system to gain a perspective of the status of the overall system operations at any point in time. In various embodiments, the insights monitoring module 120 may be configured to alert the user 102 if a particular action or issue is detected within the system, which allows for the user 102 to address the action or issue promptly.

In a particular embodiment, the cloud-supported infrastructure 106 may include a transcription services module 122. According to various aspects of the present disclosure, the transcription services module 122 may be configured to transcribe (in real-time) detected/recorded spoken language as received from the mobile device 104, parse unstructured transcription text data for generating structured data, identify discrete medical data in the structured data, etc. In certain embodiments, the detected/recorded spoken language may be transcribed at various locations, such as at the mobile device 104 or at a third-party transcriber included in the remote services 108, and transcription data from these system components may transmit the transcription data to the transcription services module 122 for further processing. In one embodiment, the transcription services module 122 may be configured to receive dictated audio files or speech-to-text data from the mobile device 104 and furthermore transcribe/parse the data according to a preferred coding format. In response to the transcription services module 122 generating structured data from unstructured transcription text data, the API services 112 may transmit discrete medical information included in the structured data to one or more EHR systems. In particular embodiments, the API services 112 may periodically query the transcription services model 122 for transcription data or structured data (e.g., every second, every five seconds, every 10 seconds, on-demand, etc.), or the transcription services module 122 may push transcription data or discrete data to the API services 112 as appropriate.

In various embodiments, the transcription services module 122 may operate similarly to services such as MModal or IMO for transcribing medical information according to preferred coding formats and standards. In particular embodiments, the transcription services module 122 may be located local to the mobile device 104, within the remote services 108, or within the remote EHR servers/systems 110.

Still referring to FIG. 1, the cloud-supported architecture 106 may include a service bus relay 124, as depicted in the present embodiment. In various embodiments, the service bus relay 124 is a network tool configured to communicably connect the cloud-supported architecture 106 to remote servers, EHR systems, remote services, clients, and applications. In a particular embodiment, the service bus relay 124 may implement port forwarding (or port mapping) for directing requests received at the API services 112 to particular locations (e.g., particular EHR form locations) within EHR systems. In certain embodiments, the service bus relay may receive discrete medical data/clinical data (from transcription services 122 or traffic manager 114) in the form of AE S256 TLS encrypted data for protecting the sensitive medical data. According to various aspects of the present disclosure, the service bus relay 124 may include a bi-directional communication link or interface to the EHR systems for routing the received discrete medical data/clinical data to the corresponding EHR systems based at least on the destination designated by the authenticated user, or an identification number associated with the discrete clinical data. In some embodiments, the discrete clinical data may be transmitted to cloud-based third-party EHR APIs for actions such as creating or updating discrete clinical documentation, filing insurance claims, prescription requests, etc. It should be understood from the discussion herein that the service bus relay 124 may route discrete clinical data to one or more of the EHR systems.

Figure 2:
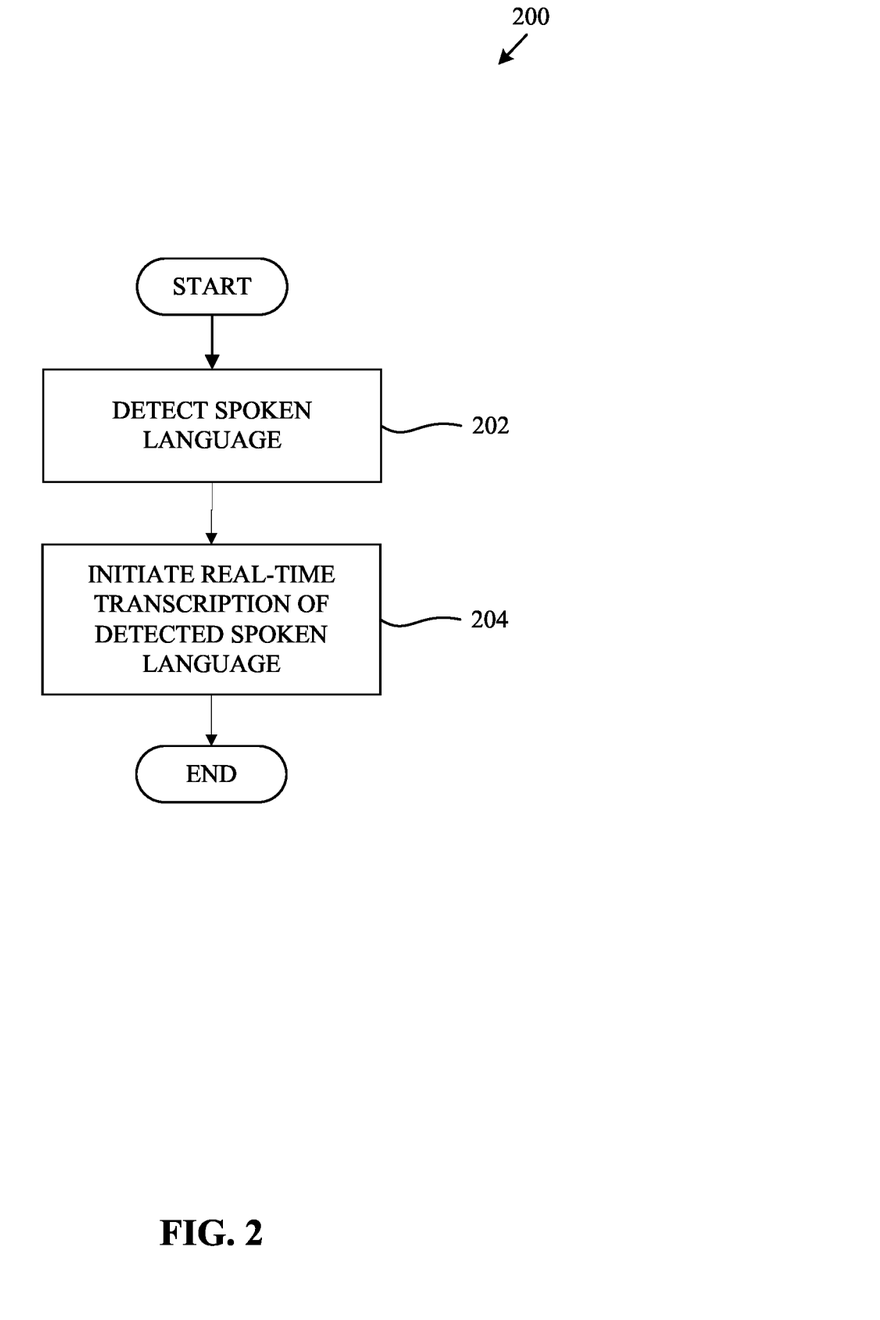
FIG. 2 is a flowchart of an exemplary transcription process, according to one aspect of the present disclosure.

Turning now to FIG. 2, a flowchart of an exemplary transcription process 200 is shown, according to one aspect of the present disclosure. As discussed herein, the present systems and methods may be implemented in various environments, such as at a doctor's office. In this exemplary environment, a doctor may conduct a medical evaluation while vocally dictating (rather than manually noting) information from the evaluation. In various embodiments, a mobile application running on his/her mobile device may be configured to detect and/or record spoken language and furthermore initiate the transcription of the spoken language, such that the relevant information from the spoken language may be converted into discrete medical data for inclusion in an electronic medical record. In this way, during the evaluation the doctor may focus directly on the patient rather than manually inputting data into an electronic health record.

According to various embodiments, this process 200 begins at step 202, where spoken language is detected via the user's mobile device. In particular embodiments, the mobile device may be a smartphone, tablet, or any computing device equipped with a microphone/speaker and networking capabilities. In certain embodiments, the mobile device may run a mobile application for initiating the transcription process. In one embodiment, the mobile application may manage patient information, such as patient identification data, insurance information, health records or evaluation history, etc., and also an archive of prior transcriptions. According to various aspects of the present disclosure, a user of the mobile application may select to begin a new transcription (by selecting a button displayed by the mobile application, via voice command or hand gesture, etc.) which, in response, may initiate the sound detection and recording functionality of the mobile device.

In various embodiments, and at step 204, in response to detecting the spoken language, the mobile device may initiate real-time transcription of the spoken language. In one embodiment, the mobile application may include instructions for automatically providing speech-to-text functionality, thus the spoken language may be transcribed in real-time as it is detected. In some embodiments, the mobile application may transmit the spoken language to a remote or third-party transcription service (e.g., transcription services 122), either in a real-time continuous data stream as the spoken language is detected, or as a packaged data payload (when language detection has concluded). In various embodiments, the system may be configured to transcribe not only healthcare information but also financial information, legal information, etc.

Figure 3:
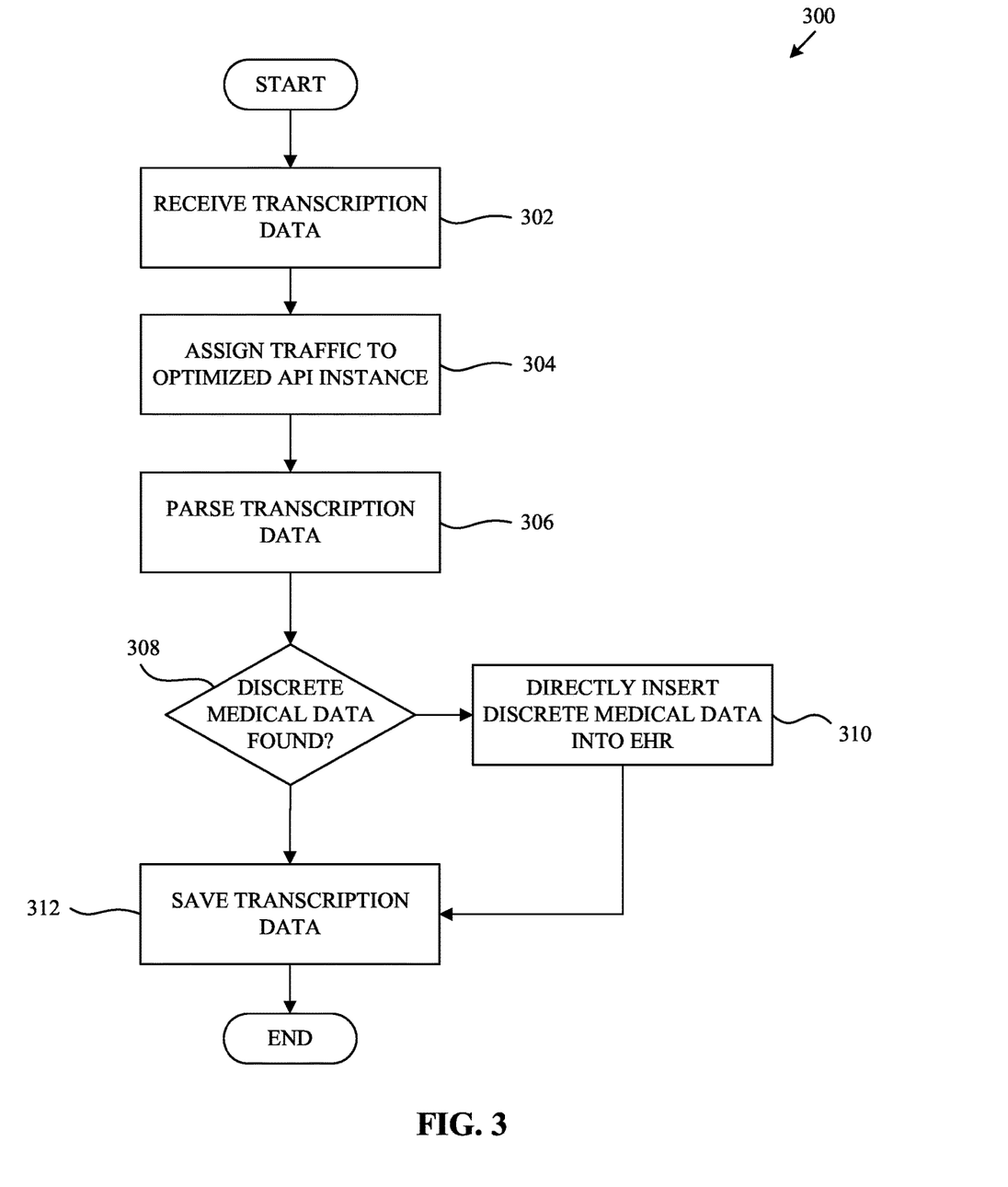
FIG. 3 is a flowchart of an exemplary EHR insertion process, according to one aspect of the present disclosure.

Referring now to FIG. 3, a flowchart of an exemplary EHR insertion process is shown, according to one aspect of the present disclosure. As discussed herein, the system may allow for spoken language of a user to be detected and transcribed, where discrete data from the spoken language transcription may be inserted into an EHR system. This exemplary process is illustrated in the present embodiment, beginning at step 302, where the cloud-supported architecture 106 receives transcription data. In one embodiment, the transcription data may be sent from the mobile device 104 or via a third-party transcription service included in the remote services 108, and the transcription data may include unstructured text data corresponding to the user's exact spoken language.

At step 304, in various embodiments and in response to receiving the transcription data at the cloud-supported architecture 106, the system determines to which API instance the transcription data (or other associated traffic) should be directed to. According to various aspects of the present disclosure, the system includes an API services module 112 including one or more API service instances, where each API service instance may be configured to process requests such as requests for processing transcription data, requests for inserting medical data into an EHR system, accessing medical data from an EHR system, etc. In some embodiments, particular API service instances may be assigned to particular EHR systems or healthcare providers, and thus the traffic manager module 114 may determine to which API instance incoming traffic should be directed (allowing for optimized computing).

In one embodiment, at step 306, the system parses the received transcription data. According to various aspects of the present disclosure, the transcription data includes unstructured text corresponding to the spoken language detected during the process associated with the discussion of FIG. 2, and the system may parse the unstructured data to identify medically relevant portions of the data (e.g., prescription information, a diagnosis, etc.) for inclusion in an EHR. In certain embodiments, the unstructured text may be parsed using one or more delineators, where the delineators may include particular words or phrases such as "prescribe," "blood pressure," "milligrams," etc. In one embodiment, the system may be configured to recognize and associate adjacent or nearby words, phrases, or values, with the delineators. For example, if the word "twenty-five" is identified before the word "milligrams," the system may combine these parsed words and separately (e.g., in a separate file or data object) represent the combination as classifiable structured data (e.g., a prescription value of 25 mg).

According to various aspects of the present disclosure, identifying classifiable structured data, such as in the example discussed above, provides the system with discrete data with which the system may further transmit to one or more EHR systems. In one embodiment, the system may determine, at step 308, if any discrete medical data is found during the step 306. If discrete data was found at step 310, the system may proceed to step 310 where the discrete data is directly inserted into one or more EHR systems (as discussed in greater detail immediately below). If, at step 308, no discrete data was found in the parsed transcription, the transcription data may be saved (at step 312) for record keeping.

Continuing with step 310, and according to various aspects of the present disclosure, the system may directly insert discrete medical data into an EHR system. In various embodiments, this step may be executed or initiated by the service bus relay 124, where the service bus relay may include an authorized connection to the target EHR system. According to various aspects of the present disclosure, the service bus relay may include a directory (or the like) of EHR systems associated with the service bus relay, as well as identifiers and EHR formatting types associated with those EHR systems. In response to receiving instructions to insert data into a particular EHR system, the service bus relay may look up a particular relay for inserting the discrete medical data into the EHR system. In some embodiments, the service bus relay may include additional information (e.g., metadata) regarding particular locations, or EHR form locations associated with a particular type of discrete data, within the EHR system to insert the discrete medical data.

In one embodiment, and at step 312, in response to inserting the discrete medical data into the one or more EHR systems, the transcription from which the discrete data was parsed may be saved.

Exemplary Application Screenshots

FIGS. 4-7 are exemplary screenshots of a mobile application at the mobile computing device 104, according to various aspects of the present disclosure. As discussed herein, a doctor may speak near or into a mobile computing device 104 during an activity such as a medical examination so that a record of the medical examination may be transcribed from the doctor's spoken language. In particular embodiments, a mobile application at the mobile device 104 may allow for this functionality.

Figure 4:
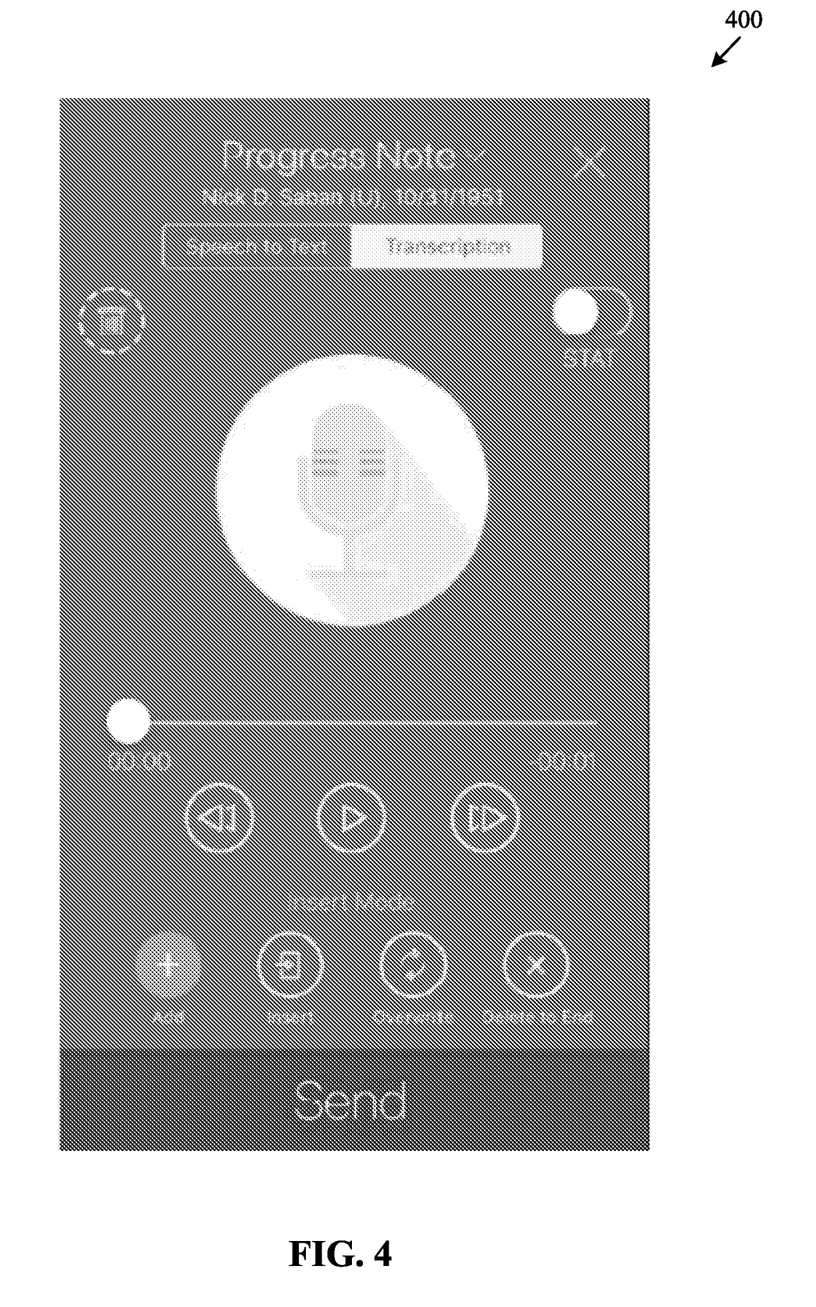
FIG. 4 is a screenshot of an exemplary mobile application, according to one aspect of the present disclosure.

Referring now to FIG. 4, an exemplary screenshot 400 of the mobile application is depicted, according to a particular embodiment. In one embodiment, the exemplary screenshot 400 may be presented to the user during an active transcription, such as when the user is actively performing a medical evaluation. As shown in the present embodiment, the exemplary screenshot 400 may allow for the doctor to begin a recording (e.g., by selecting a play button), to insert data from the transcribed recording into an EHR (e.g., by selecting an insert button), to stop the recording/transcription, etc. In some embodiments, the exemplary screenshot 400 depicts the ability for the doctor to revisit certain aspects of a recorded evaluation, such as rewinding or fast-forwarding to particular timestamps.

Figure 5:
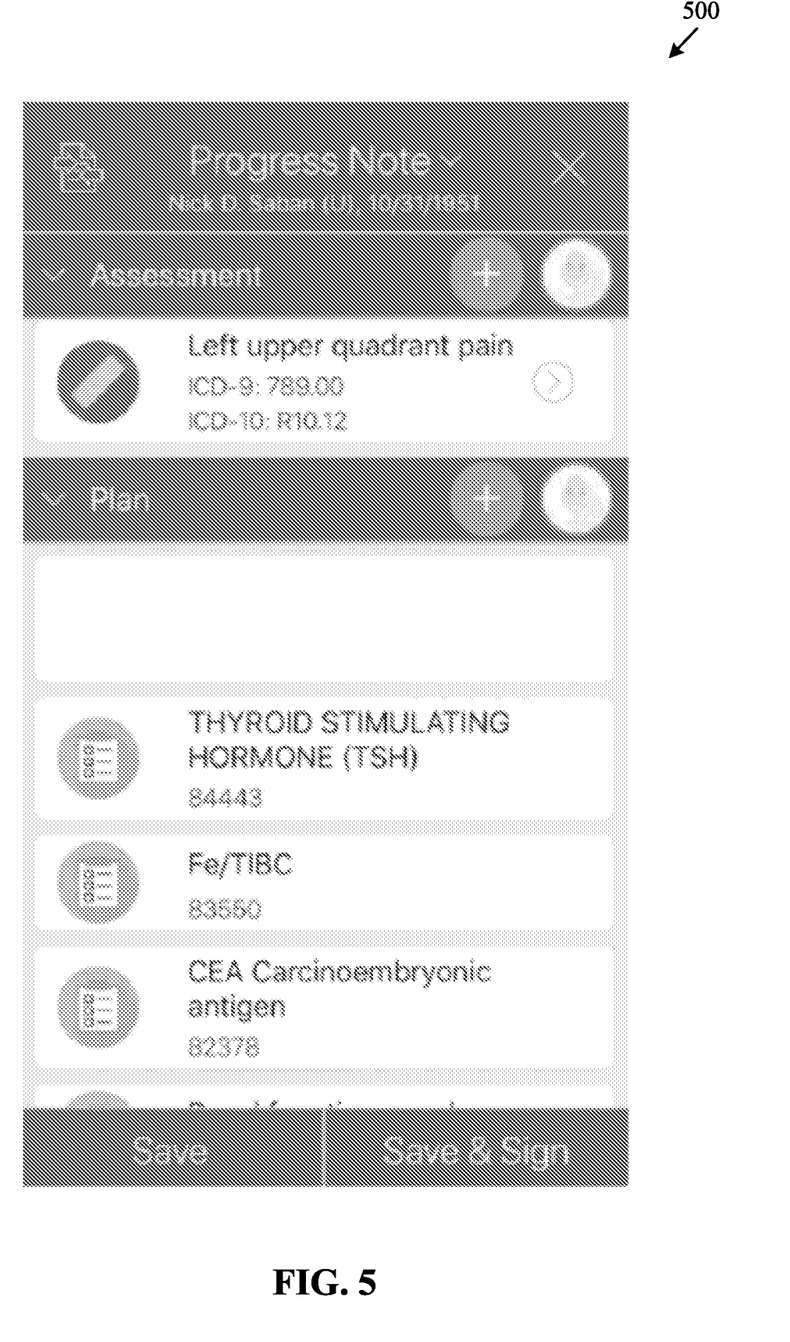
FIG. 5 is a screenshot of an exemplary mobile application, according to one aspect of the present disclosure.

In one embodiment, FIG. 5 depicts an exemplary screenshot 500 of an evaluation/assessment history screen of the mobile application. In particular embodiments, the doctor using the mobile application may also use the application for organizing and maintaining a comprehensive medical record of each patient he/she evaluates. As shown in the present embodiment, and in response to recording an evaluation/assessment, the doctor may select to "save & sign" an assessment, which may initiate a transcription of the evaluation.

Figure 6:
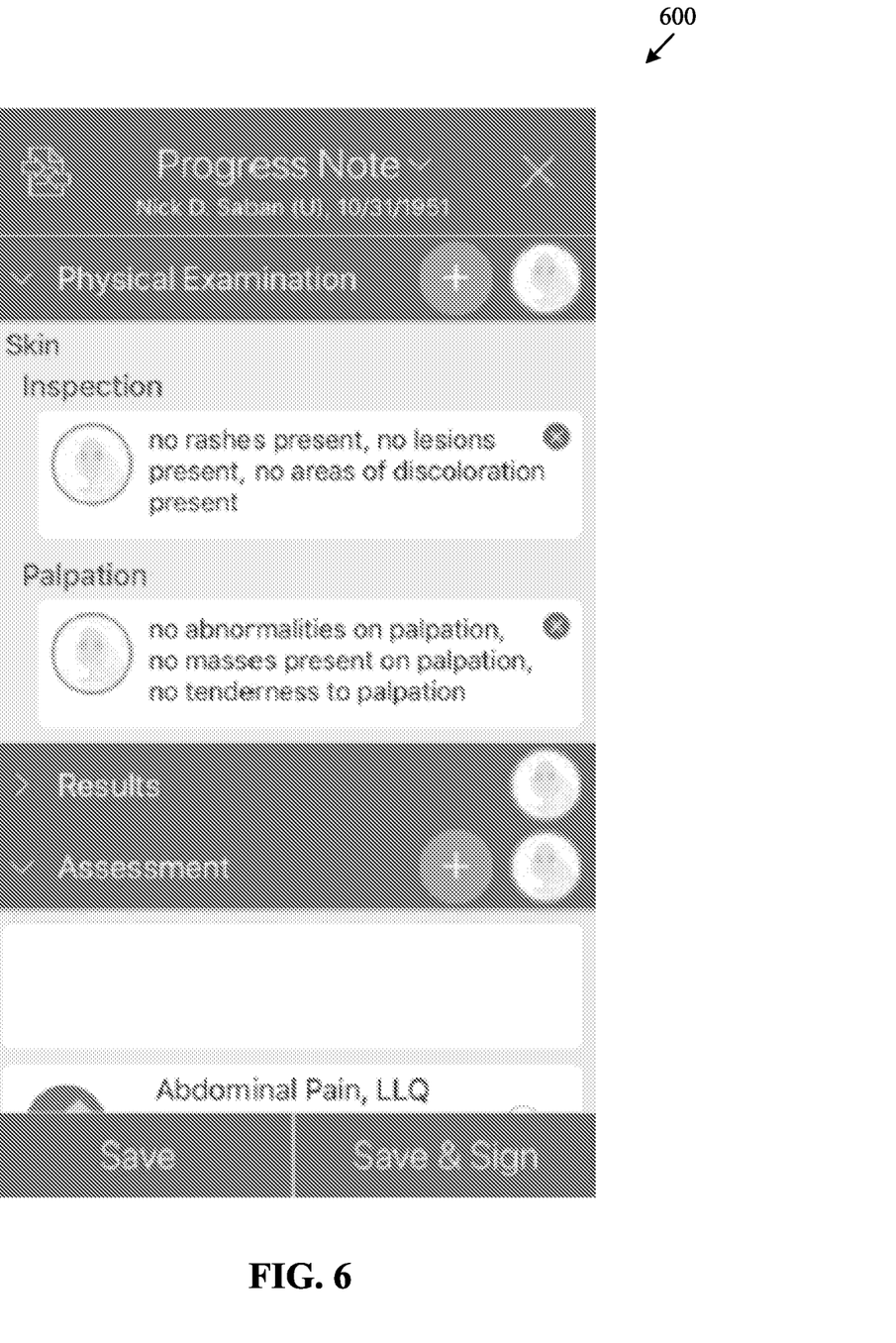
FIG. 6 is a screenshot of an exemplary mobile application, according to one aspect of the present disclosure.

According to various aspects of the present disclosure, FIG. 6 depicts an exemplary screenshot 600 of a transcription screen on the mobile application. As shown in the present embodiment, the mobile application may display transcribed text from a physical examination, where the transcribed text corresponds to the spoken language from the doctor during the examination. In various embodiments, the text displayed on the mobile application may also be real-time speech-to-text data, where the mobile application leverages natural language processing algorithms for determining which words were spoken, and also if those spoken words are associated with any medical coding terms identifiable via the natural language processing algorithms.

Figure 7:
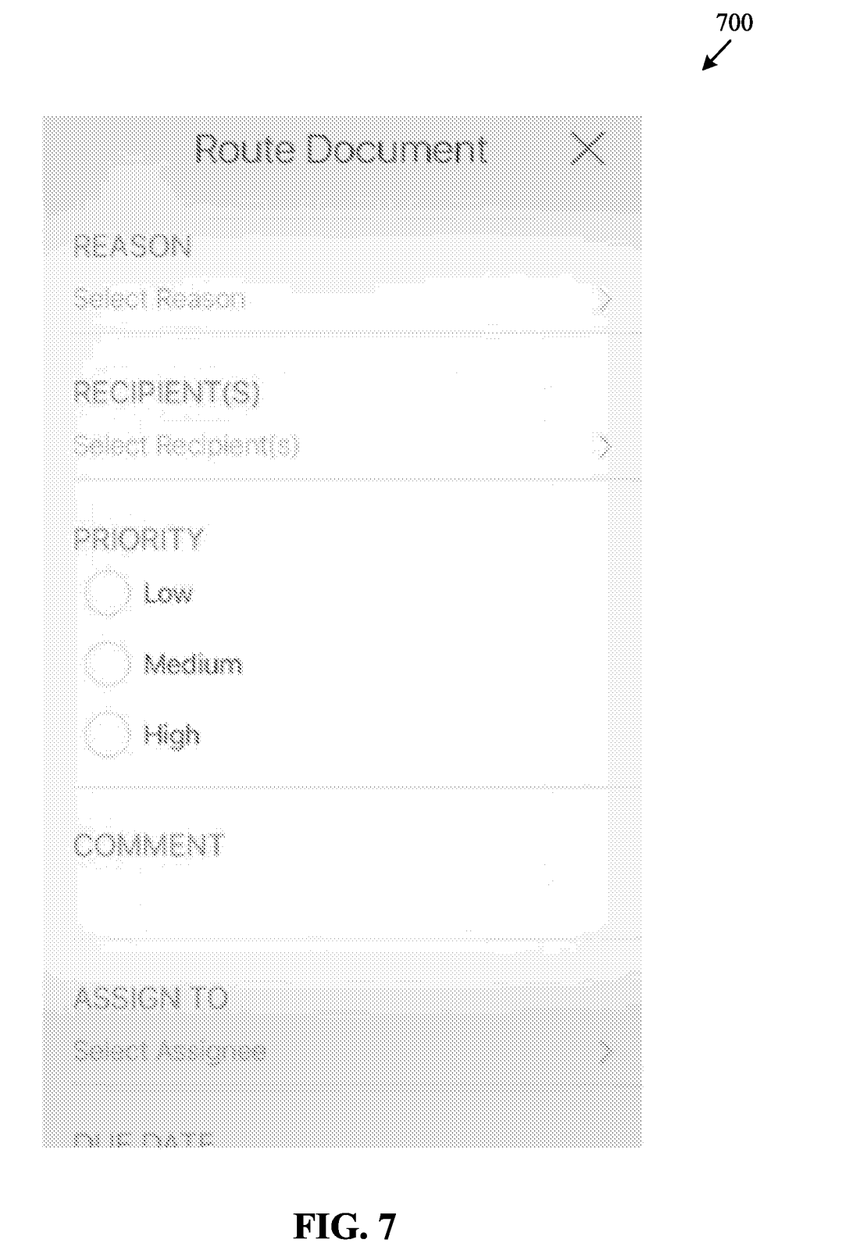
FIG. 7 is a screenshot of an exemplary mobile application, according to one aspect of the present disclosure.

Turning now to FIG. 7, an exemplary screenshot 700 is depicted illustrating a screen of the mobile application for routing particular documents from the mobile application to other systems. For example, a doctor may determine to route a transcribed evaluation to an insurance provider for updating a patient profile with the insurer, or for requesting a reimbursement. Accordingly, and as depicted in the present embodiment, the doctor may select one or more recipients for receiving the document, and the doctor may also provide information such as comments, reasons for evaluating, etc.

Additional Aspects

According to various aspects of the present disclosure, the present systems and methods may allow for the cloud-supported architecture to include a bi-directional interface to the EHR systems via the service bus relay for back-and-forth communication between the EHR systems. In one embodiment, this bi-directional interface may be proprietary or may rely on third-party tools such as the Microsoft® Azure® Service Bus Relay. In various embodiments, implementing bi-directional API services allows for API calls and requests to communicate data back-and-forth with the system modules (such as inputting discrete clinical data to the EHR and retrieving health record data from within the EHR system), rather than simply returning data in response to an API call. In some embodiments, the service bus relays (such as an Azure® Service Bus Relay and an EGR Service Bus Windows Service) may connect to the system components without a VPN.

In various embodiments, the present system may allow for vendor access to an API marketplace for accessing various EHR systems. For example, one vendor (e.g., a health care professional) may access a variety of APIs from the system, allowing the vendor to access multiple EHR systems with one username and password (or any form of credentials). In one embodiment, the vendor may expose data from multiple EHR systems into one front-end (e.g., view preexisting EHR data on a mobile application), and other vendors may create additional applications for accessing the EHR data.

In one embodiment, the system may recognize speech (e.g., via natural language processing algorithms and speech-to-text algorithms) and further convert the recognized speech to unstructured text, structured data, and discrete data. In certain embodiments, implementing natural language processing tools may allow for the system to identify terms or phrases within the recognized speech/unstructured text without human involvement (or third-party transcription), such that a user does not need to manually determine how to parse the recognized speech/unstructured data. For example, the system may train the natural language processing components with a particular medical coding format. In response to this training, the natural language processing components may identify aspects of the coding format within the recognized speech that a user might potentially be interested in capturing as structured data. In some embodiments, the natural language processing components may be trained or configured to identify various codified terms (e.g., medical coding terms), and a user may determine which coding terms for the natural language processing components to process from the recognized speech.

Accordingly, implementing natural language processing within the system may provide efficiencies when determining how to best parse unstructured data by pre-identifying potentially relevant discrete data within the unstructured data (e.g., a user does not need to manually determine how to parse the data). Furthermore, in embodiments implementing real-time speech-to-text and natural language processing, a user may indicate (within a mobile application) the particular sections of a medical examination they are dictating, which allows for the system to identify relevant coding terms associated with that particular section (e.g., a prescriptions section, a diagnosis section, etc.) as the user is speaking. According to various aspects of the present disclosure, the user-spoken audio may be converted to structured text according to the ICD10, CPT, and SNOMED coding systems via proprietary or third-party coding awareness tools. In particular embodiments, discrete data within the structured data/text may be used to update or populate EHR records or the like via the system APIs.

In particular embodiments, the present system may allow for application extensions that allow for third-parties or site portal plugins to connect to the present system for sharing information between multiple vendors. According to various aspects of the present disclosure, this may allow for the system to share, compare, and compile information to detect inconsistencies such as gaps in care or coding.

Exemplary Architecture

From the foregoing, it will be understood that various aspects of the processes described herein are software processes that execute on computer systems that form parts of the system. Accordingly, it will be understood that various embodiments of the system described herein are generally implemented as specially-configured computers including various computer hardware components and, in many cases, significant additional features as compared to conventional or known computers, processes, or the like, as discussed in greater detail herein. Embodiments within the scope of the present disclosure also include computer-readable media for carrying or having computer-executable instructions or data structures stored thereon. Such computer-readable media can be any available media which can be accessed by a computer, or downloadable through communication networks. By way of example, and not limitation, such computer-readable media can comprise various forms of data storage devices or media such as RAM, ROM, flash memory, EEPROM, CD-ROM, DVD, or other optical disk storage, magnetic disk storage, solid state drives (SSDs) or other data storage devices, any type of removable nonvolatile memories such as secure digital (SD), flash memory, memory stick, etc., or any other medium which can be used to carry or store computer program code in the form of computer-executable instructions or data structures and which can be accessed by a general purpose computer, special purpose computer, specially-configured computer, mobile device, etc.

When information is transferred or provided over a network or another communications connection (either hardwired, wireless, or a combination of hardwired or wireless) to a computer, the computer properly views the connection as a computer-readable medium. Thus, any such a connection is properly termed and considered a computer-readable medium. Combinations of the above should also be included within the scope of computer-readable media. Computer-executable instructions comprise, for example, instructions and data which cause a general purpose computer, special purpose computer, or special purpose processing device such as a mobile device processor to perform one specific function or a group of functions.

Those skilled in the art will understand the features and aspects of a suitable computing environment in which aspects of the disclosure may be implemented. Although not required, some of the embodiments of the claimed systems may be described in the context of computer-executable instructions, such as program modules or engines, as described earlier, being executed by computers in networked environments. Such program modules are often reflected and illustrated by flow charts, sequence diagrams, exemplary screen displays, and other techniques used by those skilled in the art to communicate how to make and use such computer program modules. Generally, program modules include routines, programs, functions, objects, components, data structures, application programming interface (API) calls to other computers whether local or remote, etc. that perform particular tasks or implement particular defined data types, within the computer. Computer-executable instructions, associated data structures and/or schemas, and program modules represent examples of the program code for executing steps of the methods disclosed herein. The particular sequence of such executable instructions or associated data structures represent examples of corresponding acts for implementing the functions described in such steps.

Those skilled in the art will also appreciate that the claimed and/or described systems and methods may be practiced in network computing environments with many types of computer system configurations, including personal computers, smartphones, tablets, hand-held devices, multiprocessor systems, microprocessor-based or programmable consumer electronics, networked PCs, minicomputers, mainframe computers, and the like. Embodiments of the claimed system are practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

An exemplary system for implementing various aspects of the described operations, which is not illustrated, includes a computing device including a processing unit, a system memory, and a system bus that couples various system components including the system memory to the processing unit. The computer will typically include one or more data storage devices for reading data from and writing data to. The data storage devices provide nonvolatile storage of computer-executable instructions, data structures, program modules, and other data for the computer.

Computer program code that implements the functionality described herein typically comprises one or more program modules that may be stored on a data storage device. This program code, as is known to those skilled in the art, usually includes an operating system, one or more application programs, other program modules, and program data. A user may enter commands and information into the computer through keyboard, touch screen, pointing device, a script containing computer program code written in a scripting language or other input devices (not shown), such as a microphone, etc. These and other input devices are often connected to the processing unit through known electrical, optical, or wireless connections.

The computer that effects many aspects of the described processes will typically operate in a networked environment using logical connections to one or more remote computers or data sources, which are described further below. Remote computers may be another personal computer, a server, a router, a network PC, a peer device or other common network node, and typically include many or all of the elements described above relative to the main computer system in which the systems are embodied. The logical connections between computers include a local area network (LAN), a wide area network (WAN), virtual networks (WAN or LAN), and wireless LANs (WLAN) that are presented here by way of example and not limitation. Such networking environments are commonplace in office-wide or enterprise-wide computer networks, intranets, and the Internet.

When used in a LAN or WLAN networking environment, a computer system implementing aspects of the system is connected to the local network through a network interface or adapter. When used in a WAN or WLAN networking environment, the computer may include a modem, a wireless link, or other mechanisms for establishing communications over the wide area network, such as the Internet. In a networked environment, program modules depicted relative to the computer, or portions thereof, may be stored in a remote data storage device. It will be appreciated that the network connections described or shown are exemplary and other mechanisms of establishing communications over wide area networks or the Internet may be used.

While various aspects have been described in the context of a preferred embodiment, additional aspects, features, and methodologies of the claimed systems will be readily discernible from the description herein, by those of ordinary skill in the art. Many embodiments and adaptations of the disclosure and claimed systems other than those herein described, as well as many variations, modifications, and equivalent arrangements and methodologies, will be apparent from or reasonably suggested by the disclosure and the foregoing description thereof, without departing from the substance or scope of the claims. Furthermore, any sequence(s) and/or temporal order of steps of various processes described and claimed herein are those considered to be the best mode contemplated for carrying out the claimed systems. It should also be understood that, although steps of various processes may be shown and described as being in a preferred sequence or temporal order, the steps of any such processes are not limited to being carried out in any particular sequence or order, absent a specific indication of such to achieve a particular intended result. In most cases, the steps of such processes may be carried out in a variety of different sequences and orders, while still falling within the scope of the claimed systems. In addition, some steps may be carried out simultaneously, contemporaneously, or in synchronization with other steps.

CONCLUSION

Aspects, features, and benefits of the claimed invention(s) will become apparent from the information disclosed in the exhibits and the other applications as incorporated by reference. Variations and modifications to the disclosed systems and methods may be effected without departing from the spirit and scope of the novel concepts of the disclosure.

It will, nevertheless, be understood that no limitation of the scope of the disclosure is intended by the information disclosed in the exhibits or the applications incorporated by reference; any alterations and further modifications of the described or illustrated embodiments, and any further applications of the principles of the disclosure as illustrated therein are contemplated as would normally occur to one skilled in the art to which the disclosure relates.

The foregoing description of the exemplary embodiments has been presented only for the purposes of illustration and description and is not intended to be exhaustive or to limit the inventions to the precise forms disclosed. Many modifications and variations are possible in light of the above teaching.

The embodiments were chosen and described in order to explain the principles of the inventions and their practical application so as to enable others skilled in the art to utilize the inventions and various embodiments and with various modifications as are suited to the particular use contemplated. Alternative embodiments will become apparent to those skilled in the art to which the present inventions pertain without departing from their spirit and scope. Accordingly, the scope of the present inventions is defined by the appended claims rather than the foregoing description and the exemplary embodiments described therein.

What is claimed is:

1. A system comprising:
a processor operatively configured to initiate generation of transcription data corresponding to spoken language; and
an application programming interface (API) system, wherein the API system comprises one or more API instances operatively configured to:
receive the transcription data from the processor;
authenticate the processor via an authentication directory based on a token included in the transcription data that uniquely identifies the processor;
parse the transcription data with one or more delineators to derive discrete data comprising classifiable medical data; and
insert the classifiable medical data into a particular memory location at an electronic health record (EHR) system according to a particular formatting standard, wherein the particular memory location corresponds to a form field in an electronic health record associated with the classifiable medical data.

2. The system of claim 1, wherein the processor is further operatively configured to transmit the spoken language to a real-time transcription service for transcribing the spoken language into the transcription data.

3. The system of claim 1, further comprising an API traffic manager for assigning tasks to the one or more API instances based on a volume of requests received from the processor.

4. The system of claim 1, wherein the EHR system comprises a remote EHR system, and wherein particular API instances of the API system access particular memory locations within the remote EHR system.

5. The system of claim 1, wherein prior to inserting the classifiable medical data into the particular memory location at the EHR system, the one or more API instances are further operatively configured to normalize the discrete data into the particular formatting standard.

6. The system of claim 1, wherein the processor is operatively connected to one or more sensors operatively configured to detect the spoken language.

7. The system of claim 1, wherein the one or more delineators are determined via one or more natural language processing algorithms trained to identify the particular formatting standard.

8. A method comprising the steps of:
receiving, at an application programming interface (API) service instance, transcription data corresponding to spoken language, wherein generation of the transcription data is initiated by a processor;

authenticating the processor via an authentication directory based on a token included in the transcription data that uniquely identifies the processor;

parsing the transcription data with one or more delineators to derive discrete data comprising classifiable medical data; and inserting the classifiable medical data into a particular memory location at an electronic health record (EHR) system according to a particular formatting standard, wherein the particular memory location corresponds to a form field in an electronic health record associated with the classifiable medical data.

9. The method of claim 8, wherein prior to receiving the transcription data at the API service instance, the processor is further operatively configured to transmit the spoken language to a real-time transcription service for transcribing the spoken language into the transcription data.

10. The method of claim 8, wherein prior to receiving the transcription data at the API service instance, an API traffic manager assigns tasks to the API service instance based on a volume of requests received from the processor.

11. The method of claim 8, wherein the EHR system comprises a remote EHR system.

12. The method of claim 8, wherein prior to inserting the classifiable medical data into the particular memory location at the EHR system, the method further comprises the step of normalizing the discrete data into the particular formatting standard.

13. The method of claim 8, wherein the processor is operatively connected to one or more sensors operatively configured to detect the spoken language.

14. The method of claim 8, wherein the one or more delineators are determined via one or more natural language processing algorithms trained to identify the particular formatting standard.

15. A non-transitory computer-readable medium comprising instructions stored thereon that, when implemented by one or more processing units executing one or more application processing interface (API) service instances, cause the one or more processing units executing the one or more API service instances to:

receive, from a mobile device processor, transcription data corresponding to spoken language, wherein the mobile device processor is operatively configured to initiate generation of the transcription data;

authenticate the mobile device processor via an authentication directory based on a token included in the transcription data that uniquely identifies the mobile device processor;

parse the transcription data with one or more delineators to derive discrete data comprising classifiable medical data; and insert the classifiable medical data into a particular memory location at an electronic health record (EHR) system according to a particular formatting standard, wherein the particular memory location corresponds to a form field in an electronic health record associated with the classifiable medical data.

16. The non-transitory computer-readable medium of claim 15, wherein prior to receiving the transcription data from the mobile device processor, the mobile device processor is further operatively configured to transmit the spoken language to a real-time transcription service for transcribing the spoken language into the transcription data.

17. The non-transitory computer-readable medium of claim 15, wherein implementing the instructions stored thereon further causes the one or more processing units executing the one or more API service instances to receive assigned tasks from an API traffic manager based on a volume of requests received from the mobile device processor.

18. The non-transitory computer-readable medium of claim 15, wherein the EHR system comprises a remote EHR system, and wherein particular API service instances of the one or more API service instances access particular memory locations within the remote EHR system.

19. The non-transitory computer-readable medium of claim 15, wherein implementing the instructions stored thereon further causes the one or more processing units executing the one or more API service instances to, prior to inserting the classifiable medical data into the particular memory location at the EHR system, normalize the discrete data into the particular formatting standard.

20. The non-transitory computer-readable medium of claim 15, wherein the one or more delineators are determined via one or more natural language processing algorithms trained to identify the particular formatting standard.

* * * * *